US00PP12819P2

(12) United States Plant Patent
Brown

(10) Patent No.: US PP12,819 P2
(45) Date of Patent: Jul. 30, 2002

(54) PETUNIA PLANT NAMED 'MP7'

(75) Inventor: Graham Noel Brown, Baulkham Hills (AU)

(73) Assignee: Nuflora International Pty. Ltd., Syndey (AU)

( * ) Notice: Subject to any disclaimer, the term of this patent is extended or adjusted under 35 U.S.C. 154(b) by 0 days.

(21) Appl. No.: 09/832,036

(22) Filed: Apr. 10, 2001

(51) Int. Cl.[7] ..... A01H 5/00
(52) U.S. Cl. ..... Plt./356
(58) Field of Search ..... Plt./356

(56) References Cited

PUBLICATIONS

UPOV–ROM GTITM Computer Database, 2001/06, GTI Jouve Retrieval Software, citation for 'MP7'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Petunia plant named 'MP7', characterized by its compact, uniform cascading and outwardly spreading plant habit; freely and continuous branching habit; small leaves; and numerous small lavender pink-colored flowers with white-colored throat and light pink-colored reverse and tube.

1 Drawing Sheet

BACKGROUND OF THE INVENTION

The present Invention relates to a new and distinct cultivar of Petunia plant, botanically known as *Petunia×hybrida*, and hereinafter referred to by the cultivar name MP7.

The new Petunia is a product of a planned breeding program conducted by the Inventor in Baulkham Hills, New South Wales, Australia. The objective of the breeding program is to create cascading Petunias with numerous small flowers with attractive flower colors. The new Petunia originated from a cross made by the Inventor in 1998 of a proprietary Petunia selection identified as X98.31 as the female, or seed parent, with a proprietary Petunia selection identified as PJ39 as the male, or pollen parent. The new Petunia was selected as a single plant from the resulting progeny by the Inventor in October, 1999, in Cobbitty, New South Wales, Australia, on the basis of its cascading habit and numerous lavender pink-colored flowers.

Asexual reproduction of the new cultivar by terminal cuttings taken in Cobbitty, New South Wales, Australia since October, 1999 has shown that the unique features of this new Petunia are stable and reproduced true to type in successive generations.

SUMMARY OF THE INVENTION

Plants of the cultivar MP7 have not been observed under all possible environmental conditions. The phenotype may vary somewhat with variations in environment such as temperature, light intensity, daylength, and fertilizer rate without, however, any variance in genotype.

The following traits have been repeatedly observed and are determined to be the unique characteristics of 'MP7'. These characteristics in combination distinguish 'MP7' as a new and distinct cultivar:

1. Compact, uniform cascading and outwardly spreading plant habit.
2. Freely and continuous branching.
3. Small leaves.

4. Numerous small lavender pink-colored flowers with white-colored throat and light pink-colored reverse and tube.

Plants of the new Petunia differ from the female parent in flower color as plants of the female parent have lighter pink-colored flowers. Plants of the new Petunia differ from the male parent in flower size and color as plants of the male parent have larger and purple-colored flowers. Plants of the new Petunia differ from its siblng cultivar, MP4, U.S. Plant patent application Ser. No. 09/832,049, filed concurrently, primarily in flower color as plants of 'MP4' have dark purple-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of three typical flowering plants of 'MP7' grown in a 24.5-cm hanging basket container and were about 14 weeks old.

The photograph at the bottom of the sheet comprises a close-up view of typical developing flower buds and flowers, lower surface of an opened flower, and lower and upper surfaces of typical leaves of 'MP7'.

DETAILED BOTANICAL DESCRIPTION

The following observations, measurements and comparisons describe plants grown in Lompoc, Calif., under commercial practice during the summer and autumn in a polycarbonate-covered greenhouse with day temperatures about 24 to 29° C., night temperatures about 16 to 18° C. and light levels about 5,000 to 9,000 foot-candles. Three cuttings were planted in 24.5-cm hanging basket containers and grown for about 14 weeks. In the following description, color references are made to The Royal Horticultural Society Colour Chart, 1995 edition, except where general terms of ordinary dictionary significance are used.

Botanical classification: *Petunia×hybrida* cultivar MP7.

Parentage:

*Female parent.*—Proprietary Petunia selection identified as X98.31, not patented.

*Male parent.*—Proprietary Petunia selection identified as PJ39, not patented.

Propagation:

*Type cutting.*—Terminal vegetative cuttings.

*Time to initiate roots.*—About 14 days at 22° C.

*Time to develop roots.*—About 28 days at 22° C.

*Root description.*—Fine, fibrous, white.

*Rooting habit.*—Freely branching, dense.

Plant description:

*Form.*—Annual flowering plant; indeterminate; initially upright, then cascading and outwardly spreading; uniform; plants eventually becoming hemispherical to spherical in shape. Viscid and glandular pubescent. Freely basal branching with about 6 main lateral branches per plant with potentially lateral branches forming at every node.

*Usage.*—Appropriate for hanging baskets, window boxes, patio containers and landscape applications.

*Plant height.*—About 22 cm.

*Plant diameter.*—About 32 cm.

*Vigor.*—Moderately vigorous.

*Lateral branches.*—Length: About 34 cm. Diameter: About 2.75 mm. Internode length: About 1.9 cm. Texture: Pubescent. Color: 144B.

*Foliage description.*—Leaves simple, generally symmetrical and long-persisting; opposite. Quantity per later branch: About 50. Length: About 3.5 cm. Width: About 2.8 cm. Shape: Elliptic to almost oval. Apex: Broadly acute to rounded. Base: Attenuate. Margin: Entire. Texture: Smooth, glabrous; glandular, viscid. Venation pattern: Arcuate. Color: Young foliage, upper surface: 146A. Young foliage, lower surface: 146B. Mature foliage, upper surface: 146A. Mature foliage, lower surface: 146A. Venation, upper surface: 146D. Venation, lower surface: 146B. Petiole length: About 1 cm. Petiole diameter: About 2 mm. Petiole color: 146C.

Flower description:

*Flower type and habit.*—Small salverform flowers; flowers face mostly upward or outward; single, axillary. Flowers persistent. Very freely flowering, typically about 150 open flowers and flower buds per plant.

*Natural flowering season.*—Long day responsive; spring until frost in the autumn; flowering continuous.

*Flower longevity on the plant.*—About 7 to 10 days in the greenhouse.

*Fragrance.*—Not detected.

*Flower size.*—Diameter: About 3.2 cm. Tube length: About 2.5 cm. Throat diameter, distal end: About 8 mm. Tube diameter, proximal end: About 3 mm.

*Flower buds* (*showing color*).—Length: About 2.75 cm. Diameter: Apex: About 5 mm. Base: About 3 mm. Shape: Elongated oblong with slightly ruffled apices Color: Towards base, 147D, towards apex, 75D.

*Corolla.*—Arrangement/appearance: Single whorl of five petals, fused into flared trumpet with distinct clefts between petal lobes. Petal length from throat: About 1.6 cm. Petal width: About 1.2 cm. Petal shape: Roughly spatulate or fan-shaped. Petal apex: Rounded to very broadly acuminate. Petal margin: Entire. Petal texture: Smooth, velvety. Color: Petal, upper surface, when opening: 73A. Petal, lower surface, when opening: 75D. Petal, upper surface, fully opened: 78B, fading to 78C with subsequent development. Petal, lower surface, fully opened: 75D. Flower throat (inside): 155A. Flower tube (outside): 75D. Venation, upper and lower petal surfaces: 144D. Venation, throat: 144C. Venation, tube: 144D.

*Sepals.*—Arrangement/appearance: Single whorl of five sepals fused at base, star-shaped. Length: About 1.1 cm. Width: About 3.25 mm. Shape: Strap-like; narrow, elongate. Apex: Rounded. Margin: Entire. Texture, both surfaces: Pubescent. Color: Upper surface: 137A. Lower surface: 137C.

*Peduncles.*—Length: About 3.5 cm. Width: About 1.4 mm. Angle: About 45° to the stem. Strength: Moderately strong; wiry. Texture: Pubescent. Color: 144B.

*Reproductive organs.*—Stamens: Quantity/arrangement: Five, adnate to corolla tube. Anther shape: Ovoid. Anther length: About 1 mm. Anther color: 155A. Pollen amount: Scarce. Pollen color: 156D. Pistils: Quantity: One. Pistil length: About 2 cm. Stigma shape: Flat, slightly bi-lobed. Stigma color: 144C. Style length: About 1.7 cm. Style color: 149D. Ovary color: 144B.

*Seed.*—Seed production has not been observed.

Disease/pest resistance: Plants of the new Petunia have not been noted to be resistant to pathogens or pests common to Petunia.

It is claimed:

1. A new and distinct cultivar of Petunia plant named 'MP7', as illustrated and described.

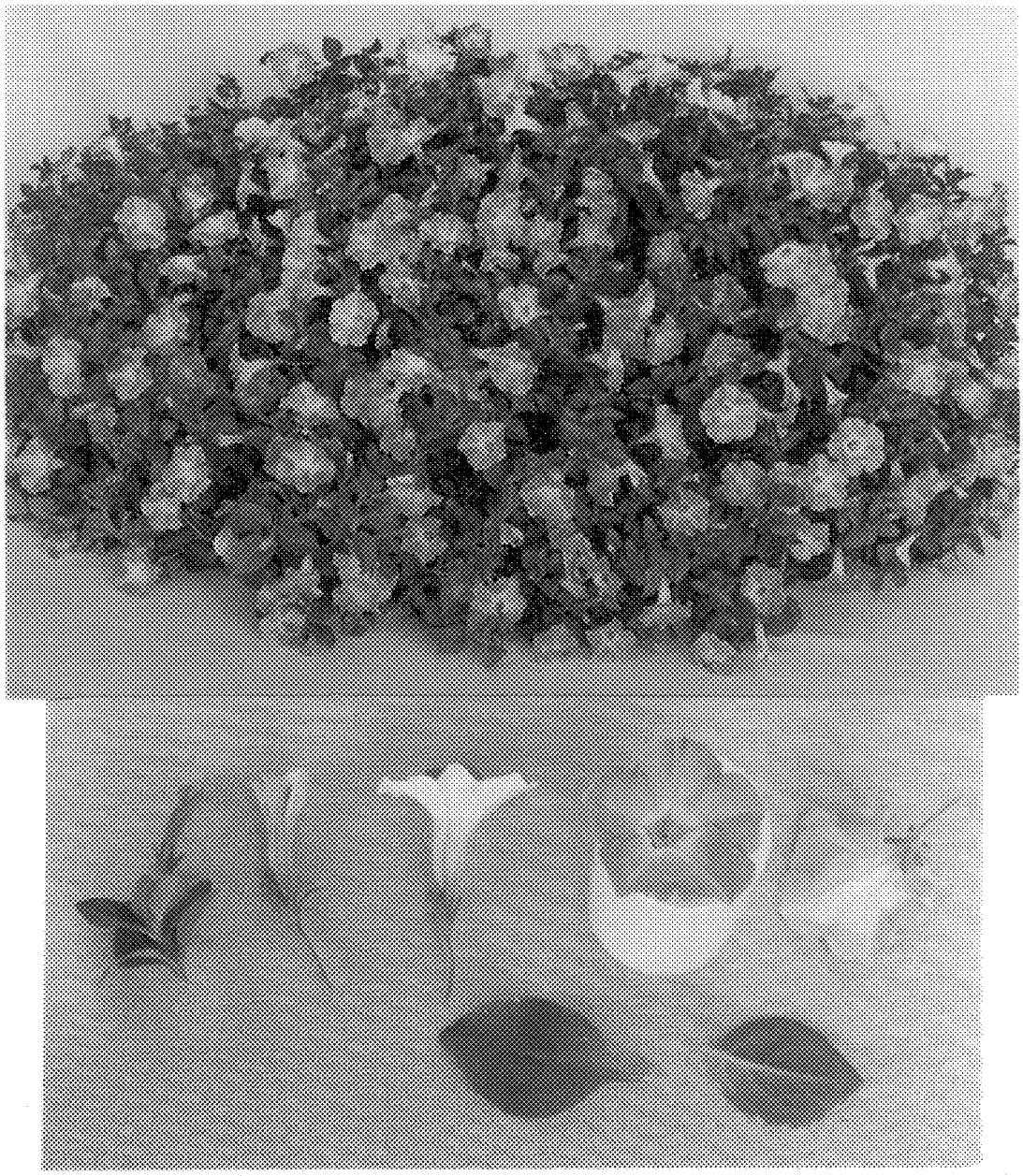

* * * * *